(12) United States Patent
Geesbreght et al.

(10) Patent No.: US 9,636,023 B2
(45) Date of Patent: May 2, 2017

(54) PORTABLE RAPID VITAL SIGN APPARATUS AND METHOD

(71) Applicants: John M. Geesbreght, Fort Worth, TX (US); Darrell D. Dial, Fort Worth, TX (US)

(72) Inventors: John M. Geesbreght, Fort Worth, TX (US); Darrell D. Dial, Fort Worth, TX (US)

( * ) Notice: Subject to any disclaimer, the term of this patent is extended or adjusted under 35 U.S.C. 154(b) by 45 days.

(21) Appl. No.: 14/645,606

(22) Filed: Mar. 12, 2015

(65) Prior Publication Data

US 2015/0257658 A1 Sep. 17, 2015

Related U.S. Application Data

(60) Provisional application No. 61/951,755, filed on Mar. 12, 2014.

(51) Int. Cl.
*A61B 5/0205* (2006.01)
*A61B 5/1455* (2006.01)
(Continued)

(52) U.S. Cl.
CPC ........ *A61B 5/02055* (2013.01); *A61B 5/0022* (2013.01); *A61B 5/0205* (2013.01);
(Continued)

(58) Field of Classification Search
CPC . A61B 5/02055; A61B 5/0022; A61B 5/0205; A61B 5/02416; A61B 5/14551;
(Continued)

(56) References Cited

U.S. PATENT DOCUMENTS

| 5,724,025 A | 3/1998 | Tavori |
|---|---|---|
| 5,931,791 A | 8/1999 | Saltzstein et al. |

(Continued)

FOREIGN PATENT DOCUMENTS

| WO | 2013148753 A1 | 10/2013 |
|---|---|---|
| WO | PCT/US2015/20243 | 6/2015 |

OTHER PUBLICATIONS

Sotera Wireless, ViSi Mobile System product website, 2 pages www.visimobile.com/overview.

(Continued)

*Primary Examiner* — Michael Kahelin
*Assistant Examiner* — Minh Duc Pham
(74) *Attorney, Agent, or Firm* — Whitaker Chalk Swindle & Schwartz PLLC; Stephen S. Mosher

(57) ABSTRACT

A portable, cuffless instrument and system for providing rapid measurements of vital signs of a patient undergoing trauma from illness or injury comprising a portable instrument connectable via contact sensors to the patient to produce a vital sign data set including blood pressure, pulse, blood oxygen saturation, and body temperature. The instrument preferably includes wireless communication capability in a network and system including a remote server, database, and processing capability to provide access to electronic medical records, to analyze the vital signs data, report preliminary diagnoses to a care giver, including listing chronologically vital sign data for trends.

19 Claims, 7 Drawing Sheets

(51) Int. Cl.
  *A61B 5/00* (2006.01)
  *A61B 5/024* (2006.01)
  *A61B 5/01* (2006.01)

(52) U.S. Cl.
  CPC ...... *A61B 5/02416* (2013.01); *A61B 5/14551* (2013.01); *A61B 5/7275* (2013.01); *A61B 5/0008* (2013.01); *A61B 5/01* (2013.01); *A61B 5/02438* (2013.01); *A61B 5/14552* (2013.01); *A61B 5/6826* (2013.01); *A61B 5/6898* (2013.01); *A61B 5/743* (2013.01); *A61B 2560/0462* (2013.01)

(58) Field of Classification Search
  CPC ......... A61B 5/275; A61B 5/0008; A61B 5/01; A61B 5/02438; A61B 5/14552; A61B 5/6826; A61B 5/6898; A61B 5/743; A61B 5/0462
  USPC ...................................................... 600/301
  See application file for complete search history.

(56) References Cited

U.S. PATENT DOCUMENTS

| | | | |
|---|---|---|---|
| 6,102,856 | A | 8/2000 | Groff et al. |
| 6,290,652 | B1 | 9/2001 | Wellnhofer |
| 6,409,660 | B1 | 6/2002 | Sjoqvist |
| 6,454,705 | B1 | 9/2002 | Cosentino et al. |
| 6,786,406 | B1 | 9/2004 | Maningas |
| 8,086,301 | B2 | 12/2011 | Cho et al. |
| 8,283,620 | B2 | 10/2012 | Raynor et al. |
| 8,465,424 | B2 | 6/2013 | Aggarwal |
| 8,550,996 | B2 | 10/2013 | Parshuram et al. |
| 8,591,411 | B2 | 11/2013 | Banet et al. |
| 8,594,776 | B2 | 11/2013 | McCombie et al. |
| 8,641,636 | B2 | 2/2014 | Chang |
| 8,652,038 | B2 | 2/2014 | Tran et al. |
| 8,666,782 | B2 | 3/2014 | Thierman |
| 2006/0009698 | A1 | 1/2006 | Banet et al. |
| 2006/0084878 | A1* | 4/2006 | Banet ............ A61B 5/0205 600/485 |
| 2007/0167844 | A1 | 7/2007 | Asada et al. |
| 2007/0276632 | A1* | 11/2007 | Banet ............ A61B 5/021 702/187 |
| 2008/0097178 | A1 | 4/2008 | Banet et al. |
| 2008/0221399 | A1* | 9/2008 | Zhou ............ A61B 5/021 600/301 |
| 2008/0235058 | A1 | 9/2008 | Friedman et al. |
| 2009/0023422 | A1 | 1/2009 | MacInnis et al. |
| 2011/0213227 | A1 | 9/2011 | Ziv et al. |
| 2012/0143018 | A1 | 6/2012 | Skidmore et al. |
| 2012/0265026 | A1 | 10/2012 | Shenasa et al. |
| 2012/0330681 | A1 | 12/2012 | Olalekan |
| 2013/0014706 | A1 | 1/2013 | Menkes |
| 2013/0303870 | A1 | 11/2013 | Satish et al. |
| 2014/0077946 | A1 | 3/2014 | Tran |
| 2014/0243612 | A1 | 8/2014 | Li et al. |
| 2015/0018649 | A1 | 1/2015 | Lisogurski et al. |

OTHER PUBLICATIONS

Tamura, Toshiyo, et al., Wearable Photoplethysmorgraphic—Past and Present, Electronics 2014 (journal), Apr. 23, 2014, 21 pages, Apr. 23, 2014, © 2014, Basel, Switzerland.
Kim, June Young, Design of Infrared Sensor Based Measurement System for Continuous Blood Pressure Monitoring Device, Electrical Engineering Project Report (article); 12 pages, Jan. 1, 2016, University of Minnesota.
Gao, Tia, et al., Vital Signs Monitoring and Patient Tracking Over a Wireless Network, John Hopkins Technical Digest (article), 9 pages, vol. 27, No. 1, 2006.
Wikipedia, Continuous Noninvasive Arterial Pressure (article), 9 pages, Jan. 5, 2015.
Schulz, Sandra L., Oxygen Saturation Monitoring by Pulse Oximetry (article), AACN Procedure Manual for Critical Care, Fourth Addition, 6 pages, © 2001.
Imholz, Ben P. M., et al., Fifteen Years Experience with Finger Arterial Pressure Monitoring: Assessment of the Technology (article), 15 pages, © 2015, Oxford University Press, Journals, vol. 38, Issue 3.
Buxbaum, Peter, Vital Signs Algorithms (article), Military Medical/CBRN Technology, 3 pages, Jan. 23, 2014.
Ristuccia, Heather L. et al., Incremental Bias in Finapres Estimation of Baseline Blood Pressure Levels Over Time (article), 8 pages, Oct. 23, 1996, Hypertension http://hyper.ahajournals.org.
Andriessen, Peter, et al., Feasability of Noninvasive Continuous Finger Arterial Blood Pressure Measurements in Very Young Children, Aged 0-4 years (article), Pediatric Research, 10 pages, Jan. 8, 2008 www.nature.com/pr/journal.
Pompei, Francesco, Physics, Physiology and Serendipity of Temporal Artery Thermometry (article), Ask The Expert, 10 pages.
Shaltis, P., et al., A Hydrostatic Approach to Cuffless Blood Pressure Monitoring (article), 4 pages, Dept. of Mechanical Engineering, MIT, Cambridge MA, Massachusetts General Hospital, Boston, MA.
Woods, Ben, Wello: The Health Monitor that Could Change Your Life, or Just Your Workout (article), 5 pages, Mar. 6, 2014.
Digital and Automatic Wrist BP Monitor, Website, 2 pages, © 2015 www.concordhealthsupply.com/Product Details.
Cardiac Direct product website, Welch Allyn LXi Spot Vital Signs, 3 pages © 2013 www.cardiacdirect.com.
Zoll Medical Corporation product website, Propaq M, 2 pages, © 2013.
Medical Resources product website, Welch Allyn Propaq LT Monitor, 2 pages, © 2006, 2007 2008 2009 www.medicalresources.com.
Remote Diagnostic Technoiogies Limited product website, EMS/Pre-Hospital, Tempus Pro™, 5 pages, © 2014 www.rdtld.com/emspre-hospital.
Remote Diagnostic Technologies Limited product website. Military, Tempus Pro™, 3 pages, © 2014 www.rdtld.com/military.
Nihon University College of Engineering product website, Novel Blood Pressure Monitor, 2 pages, © 2012 www.ee.ce.nihon-u.ac.jp.
ViATOM Technology product website, Checkme™, Health Monitor, 6 pages, © 2014 www.viatomtech.com.
Spacetabs Healthcare, webpages for "qube™", Patient Monitor, 3 pages, © 2013 www.spacelabshealthcare.com.
MDDI Medical Device and Diagnostic Industry News, Sotera Wireless Seeks Continuous Vital Sign Monitoring, (article), 4 pages, May 5, 2014 www.mddionline.com/article/soter-wireless-manufacturer-year.
X, Zhou et al., Integration of Information Technology, Wireless Networks, and Personal Digital Assistants far Triage and Casualty, webpages, 2 pages, Telemed J E. Health, Aug. 12, 2006 www.ncbi.nlm.nih.gove/pubmed/16924219.
WelchAllyn NPL, Spot Vital Signs® Devices, website, 2 pages, Dec. 31, 2014 intl.welchallyn.com/apps/products.
Mobile Vital Signs Monitoring: Everyone, Everywhere, LionsGate Technologies, A Technology Whitepaper, 5 pages, Mar. 31, 2013 www.LGTmedical.com.

* cited by examiner

PORTABLE RAPID VITAL SIGN APPARATUS AND METHOD

RELATED APPLICATIONS

The present application claims priority to U.S. Provisional Patent Application No. 61/951,755 filed Mar. 12, 2014 by the same inventors entitled PORTABLE RAPID VITAL SIGN APPARATUS AND METHOD.

BACKGROUND OF THE INVENTION

1. Field of the Invention

The present invention generally relates to devices for monitoring or measuring vital signs of patients in a treatment setting, and more particularly to a portable, self-contained device capable of rapidly measuring selected key vital signs of an injured or sick patient in one operation in an emergency or triage setting.

2. Background of the Invention and Description of the Prior Art:

Vital physiological signs that are key measures of the state of health of medical patients, especially in emergency situations include blood pressure and pulse rate, blood oxygen saturation level, and temperature. The measurements of these four parameters provide important indicators of a patient's condition along with the patient's description thereof. Blood pressure, typically measured by a sphygmomanometer and a stethoscope, provides the pressure values when the heart contracts (systolic) and when the heart relaxes (diastolic), a reliable indicator of the health of the blood circulatory system and its condition or state at the time of the measurement. Pulse rate is a measure of the number of times the heart beats per minute.

Blood hemoglobin saturation level, measured non-invasively with a pulse oximeter, is a measure of the proportion of oxygen bound up in the blood hemoglobin. This measurement is an indirect indicator of the oxygenation efficiency of the respiratory system ("respiratory sufficiency") of a patient. The body temperature of a patient, traditionally measured with a thermometer, indicates whether the ability of the body to eliminate or generate heat to maintain the correct temperature is functioning correctly. Temperature is another primary indicator of the body's condition or state when experiencing injury or illness.

Patients brought into triage in emergency room settings, or requiring assessment of injuries or illness at the scene of an accident or the onset of acute or severe symptoms, need to have their vital signs measured accurately, rapidly, and in some cases repeatedly, to provide an initial assessment of the patient's condition. In most situations, the key vital sign measurements are blood pressure, pulse rate, the saturation of oxygen in the blood (pulse oximetry), and the temperature. Traditionally, these measurements were obtained manually using separate instruments, and usually not all at the same time. Often, the complete vital sign data is not available at the time the physician arrives at the bedside to begin the examination and diagnosis, and to assess the patient's need for treatment. More recently, but typically in patient care areas other than emergency or transport facilities, electronic monitor equipment installed next to the patient's bedside is connected to the patient through cables and wiring for taking continuous measurements and displaying them to the care givers. Such monitoring equipment is unwieldy and limits the ability of the patient to shift position or to be moved. These shortcomings make such monitoring unsuitable in emergency or triage situations where taking vital signs rapidly and with minimum operating inconvenience is crucial to the treatment assessment and delivery required in these situations. This is equally evident if not more so in the pre-hospital care setting. What is needed is a rapid way to measure these vital sign parameters in a single process and to enable such rapid measurements repetitively to establish trend lines, thus facilitating processing of the patient as rapidly as possible into the appropriate care environment.

Another problem with the traditional methods, whether using manual instruments or the conventional bedside monitors, is the lack of the ability to quickly and automatically transmit vital sign data to an electronic medical record (EMR) and to quickly access those patient's records, to facilitate performing a preliminary diagnostic analysis, virtually as soon as the vital signs are obtained. The lack of such information close to the time the vital signs are known could impair the ability to provide the correct initial treatment, and perhaps even mean the difference between life and death of a patient in a severe trauma circumstance. What is needed is a way to report or convey this information to a physician as a complete set of both initial and repetitive data, to enable access to this type of information with minimal delay, and preferably to make the data known at the same time that the vital signs are known.

Of further great functional importance is the ability, typically not readily available, is the listing of all available vital sign data displayed chronologically from the time vital signs were taken pre-hospital through the entire patient journey including the emergency department, surgery, recovery, intensive care unit (ICU), etc. What is needed is a system and suitable device to have vital sign data immediately available to the caregiver at all times, accompanied by the time the data was taken and other pertinent information.

SUMMARY OF THE INVENTION

Accordingly, in one embodiment there is provided a portable instrument for providing rapid measurements of vital signs, comprising a handheld, cuffless device operable by contact during assessment of a patient undergoing health trauma to establish a vital sign data set; an assembly of sensors in the device for measuring and outputting measurement values for blood pressure, pulse, blood oxygen saturation, and body temperature; a processor in the device operable under programmed control to receive and process the measurement values output by the sensors and produce a vital signs data set; and a wireless interface coupled to the processor for transmitting the vital sign data set to an electronic medical record in a remote database for display of the vital sign data on a single display screen to medical personnel.

In other aspects, the invention includes a display controlled by the processor for reading out the vital sign data set, and a single housing having finger stations for sensing by contact the patient's blood pressure, pulse, blood oxygen saturation, and body temperature.

In another aspect, the invention includes a cuffless sensor for measuring by contact the patient's systolic and diastolic blood pressure, a pulse oximeter sensor for measuring by contact the patient's pulse and blood oxygen saturation, a thermometer for measuring by contact the patient's body temperature, and at least one analog-to-digital convertor circuit for converting data output by each sensor for processing by the processor.

In another aspect, the invention includes optical proximity sensors operable to detect changes in blood flow through the capillary bed of a patient's finger tip, and operable to detect body temperature of a temporal artery.

In another aspect the invention includes a programmable central processing unit including, a memory for program storage, and at least program instructions for processing the sensor data and controlling the wireless interface. The wireless interface may be controlled by the processor operable according to a communications protocol to communicate with a remote server via a wireless network.

In a second embodiment, the invention provides a system for assisting in emergency medical diagnosis comprising the portable instrument of the first embodiment and a server connected to a program memory and a database for electronic medical records, and operable in a medical facility network of caregiver work stations and at least one emergency room workstation.

In another aspect, the system includes diagnostic analysis algorithms stored in the program memory for providing preliminary diagnosis alternatives derived from the sensor data set and the medical history data set, a selection of standard vital sign profile charts stored in the program memory and accessible during processing of the sensor data set and the medical history data set, and may include program instructions operable in the processor of the server to compare the vital sign data sets with standard vital sign profile charts and the medical history data set of the patient to produce preliminary diagnostic possibilities for the patient connected to the portable instrument.

In other aspects, the system may include caregiver workstations having a first program accessible from the caregiver work station for analyzing initial and subsequent vital sign data obtained at intervals of time by the portable instrument to enable identification of trends in the vital sign data, and a second program in the caregiver work station for displaying in a single screen display to a medical practitioner trends over time in both the vital sign data and the patient's historical data.

DETAILED DESCRIPTION OF THE INVENTION

Introduction

Figure 1:
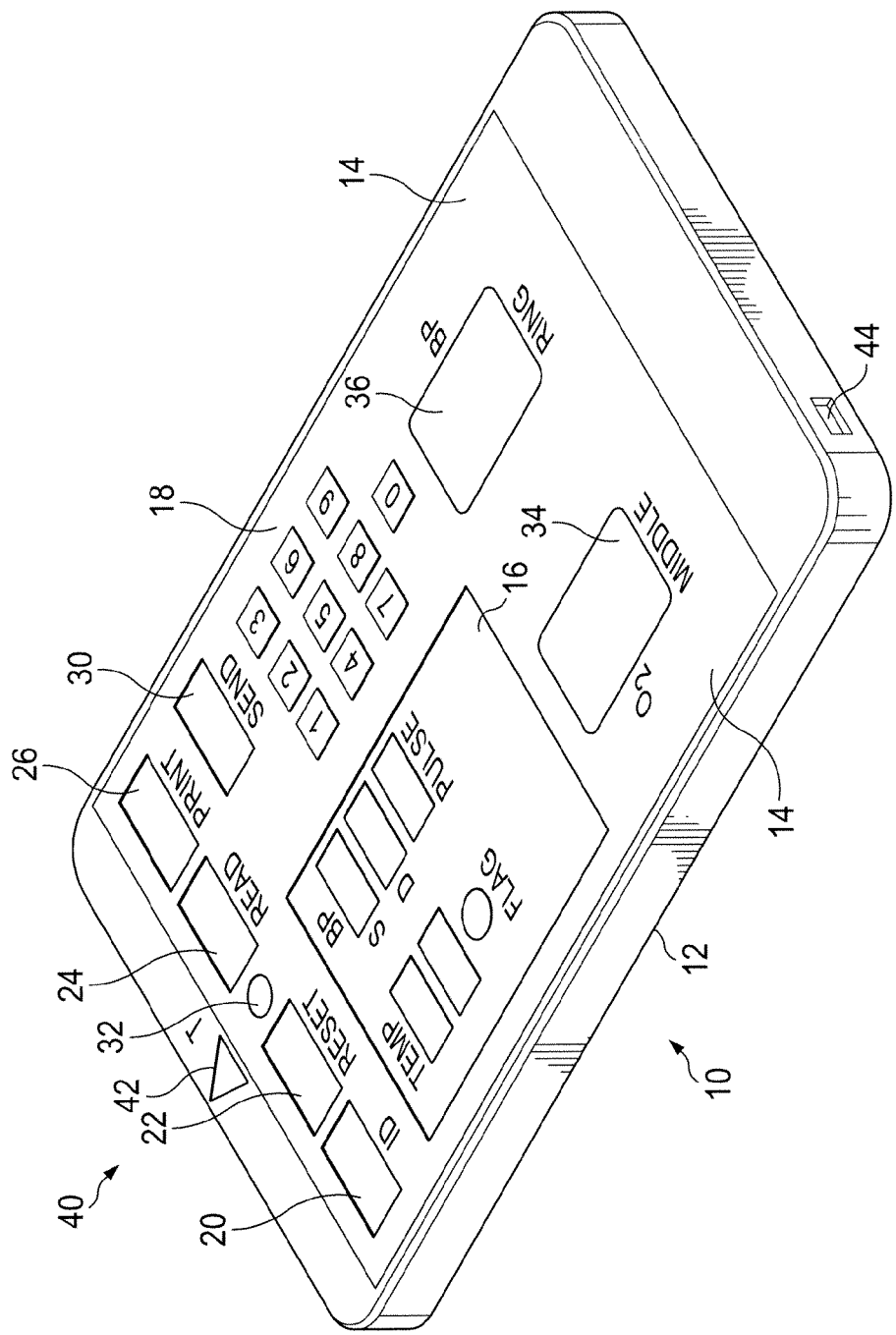
FIG. 1 illustrates one embodiment of an RVS device for measuring vital signs according to the present invention.

A medical diagnostic device and system that advances the state of the art is disclosed. The system, in broad terms includes a portable or handheld rapid vital signs ("RVS") instrument that is operable in contact with a patient undergoing evaluation to quickly produce a vital sign data set; a communications interface in the vital signs instrument for wirelessly connecting and communicating with a database via a remote server over a network; a depository of patient medical history records in the database and accessible via a server connected to the network for providing a medical history data set; and a processor in communication with the rapid vital signs instrument and the database that may be operable in some embodiments to apply selected algorithms to the vital sign and the medical history data sets to produce a preliminary diagnosis of the patient connected to the rapid vital signs instrument.

The concept of the invention may be considered as a precursor to a system of initial diagnoses that relies on accurate vital signs data and algorithms for analysis of the vital signs data, the circumstances and appearance of the patient, and other patient medical record data to determine most likely avenues for treatment and/or further tests. When a patient is brought into an emergency room time is often of the essence, and processing of incoming cases is often complicated by the number of patients awaiting examination and evaluation. The present invention is directed toward apparatus, and systems and methods for accurate and rapid assessment and diagnosis of patient illness or injury leading to appropriate treatment as soon as possible.

The rapid vital signs instrument for use in the above described system preferably includes a processor having analog-to-digital convertors (ADC) for converting input sensor data to digital form, a memory for program and data storage, a display, programs for controlling operation of the device and its display, and a communications interface. Sensor data may be supplied to the processor from sensors, preferably configured for measuring blood pressure, pulse, blood oxygen saturation, and body temperature. Sensor data converted in the ADC is input to the processor may be processed for display, and also output via the communications interface to a physician's location in the system, generally an emergency facility. In one embodiment the RVS instrument may be enclosed in a single housing having designated contact positions for sensing the patient's blood pressure, pulse, blood oxygen saturation, and body temperature.

Although the preferred embodiment is configured as a cuffless instrument, in some embodiments an inflatable cuff device operable with the RVS device for measuring the patient's blood pressure may be attached to enable measurement of blood pressure when a patient's finger is not accessible. The housing may be configured as a small portable cabinet having a display for reading out the sensor data, a keypad or similar device for entering instructions or requests, and a wireless transmitter for sending data through a network to caregivers. In other embodiments the housing may be a small, cylindrical device that may be carried in a caregiver's pocket. In some embodiments the display may be configured or adjusted so that it is or is not readily visible to the patient. In yet other embodiments the RVS may be configured for operation with or without a cuff for measuring blood pressure.

The invention provides a single, combination RVS instrument, which may be coupled via wireless link to supply a vital signs data set to an EMR (electronic medical record) stored at a remote location. The RVS instrument (also known as a portable instrument herein) is designed to take accurate vital signs of the patient at the earliest examination point, including mobile emergency care in a field setting remote from a caregiver's location in a minimum of time. In some environments it may be possible to receive an assessment of likely problems causing the patient to need treatment. Sensors may be selected to provide vital signs data very rapidly—on the order of 15 seconds or less—as compared with conventional sphygmomanometers that typically take up to a minute or more to obtain a stable reading of blood pressure. The RVS instrument and system provides an early and fast assessment in a triage circumstance, enabling a minimum of lost time to take vital signs, assess the results, and more quickly determine the emergency care that needs to be administered as soon as possible.

Example of Use

The following outline illustrates an example of using the RVS device in an emergency room situation, beginning with the patient's entrance into the emergency facility.

I. START
   A. Patient arrives at Emergency Room (ER) or Department (ED);
   B. Check in and process the patient.
II. CHECK IN AND IDENTIFY THE PATIENT TO THE ER
   A. Issue ID and case number.
   B. Scan bar code to submit to EMR (Electronic Medical Record).
   C. Check for EMR data.
III. INPUT THE VITAL SIGNS FROM THE AMBULANCE (If in transport)
   A. Manually enter vitals signs from Pre-entry to the ER or use RVS device.
   B. Time stamp all entries.
IV. TAKE VITAL SIGNS OF THE PATIENT IN THE ER
   A. Place patient's hand on RVS sensing stage.
   B. Record the RVS vital signs data and time stamp.
   C. Verify complete and accurate data.
   D. Press SEND button to send data to doctor and EMR system.
V. VERIFY THE VITAL SIGN DATA IS CORRECT
   A. Check for accurate data collection.
   B. Add or delete data as needed.
VI. SEND VITAL SIGN DATA TO THE EMR; VERIFY RECEIPT
   A. Store the readings in memory; Print if requested.
   B. Send data to EMR; verify receipt by doctor.
VII. RETAKE THE VITAL SIGNS WITH TIME STAMP, SEND TO EMR
   A. Retake vital signs with time stamp; Repeat as needed.
   B. Select routine to run.
   C. Send data to EMR.
VIII. CLEAN OR SANITIZE THE RVS DEVICE AS REQUIRED.
   A. Apply uV radiation or other sanitizer.
   B. Prepare for next use.

DETAILED DESCRIPTION OF THE INVENTION

FIG. 1 illustrates one embodiment of an RVS device 10 (or, instrument) for measuring vital signs including blood pressure, pulse, oxygen saturation, and body temperature. The RVS device 10 may include a housing 12 and a front panel 14 containing a display 16 for reading out vital signs data, and a keypad 18 for entering data or commands. The display 16 to be described with FIG. 2 preferably includes figures for displaying the numerical values for the measured vital signs. The front panel 14 may also include designated buttons (which may be touch sensitive or physical button elements) for initiating such functions as patient ID 20, Reset 22, Read 24, Print 26, and Send 30. The ID button may provide for receiving patient identification data from a bar code reader, for example that may be connected to the RVS device 10. The Reset button 22 may be used to cancel an operation or to initialize the RVS unit 10 so that a new data set may be obtained. The Read 24 button may be used to begin reading out the vital signs data as it is being measured, after the RVS device 10 is properly placed in contact with patient's hand or fingers or forehead. The Print 26 button may be used to instruct the RVS device 10 to send the vital signs data set to a printer connected either via a wireless link (not shown) or to a system server or caregiver computer with access to a printer. The Send 30 button may be used to transmit the data set to a remote server or caregiver computer or to an EMR (Electronic Medical Record) database to add to a patient record being compiled there. An indicator light 32 may be provided on the front panel 14 of the RVS device 10 to indicate power ON, a Ready condition, a Low Power or Battery condition, etc.

The front panel 14 of the RVS device 10 preferably includes position indicia on the surface of the front panel 14 for placement of the patient's fingers to sense blood flow parameters for measurements of blood pressure, pulse, and oxygen saturation. For example, a pad 34 may be delineated as the position for measuring oxygen saturation ($O_2$) and the pad 36 may be delineated as the position for measuring systolic and diastolic blood pressure and pulse. These positions may preferably be placed close to the respective sensors (to be described). In the depicted embodiment the sensors, which are configured for sensing blood flow in the patient's finger tips—i.e., the flow of blood through the capillary bed within the finger tips—are located directly below the designated positions 34, 36. A temperature sensor 40 may be located in a forward end of the RVS device 10, as indicted by an arrowhead 42. Such a sensor 40 is preferably one that senses body temperature by contact with a patient's skin, for example on the forehead of the patient over the temporal artery just above the eyebrow. The RVS device 10 may also include a USB port connector 44 along or near an edge of the housing 12 for connecting a bar code reader, a blood pressure cuff sign, etc.

A variety of physical configurations are possible. A blood pressure cuff (not shown because it is a well-known component used with conventional devices for measuring blood pressure), which may be operable in the conventional manner in some embodiments, may be connected to the RVS device 10. For example, blood pressure may be measured with cuffs adapted to different positions on a person's upper arm, wrist, or the fingers of the person's hand. The cuff may include other types of sensors as, for example, a skin contact sensor for sensing body temperature. In all cases, the RVS device 10 includes the capability in a portable and compact instrument for rapidly measuring and reporting blood pressure, pulse rate, blood oxygen saturation, and body temperature.

The sensor portions of the RVS device 10, except in some cases the blood pressure cuff, are preferably accessed merely by touch—that is, by placing and holding the patient's hand in contact with the device. In an alternate embodiment (not shown) may be a feature for illuminating the patient's hand, or alternatively the sensor contact areas of the RVS device 10 with ultraviolet light to sanitize them. In another alternate embodiment, the RVS device 10 may be incorporated in a glove (not shown) such that the patient's hand is slipped into the glove. The glove may have a wrist gauntlet portion that includes an embedded blood pressure cuff and temperature sensor. The pulse, O2 and (alternately) temperature sensors may be included in the finger portions of the glove.

In other configurations, small finger or hand sensors may be devised that combine all of the sensor elements into a single unit. Some RVS devices 10 may be linked to a smart phone or wrist phone (not shown) equipped with an application program ("AP") for convenience. Such a configuration is compact and readily carried in a pocket by a care giver. Like the larger configurations described above, the smaller ones may include the transceiver and interface (to be described) necessary for communicating with an EMR (Emergency Medical Record) system.

In some embodiments, the wireless interface or transceiver 70, 126 (See FIGS. 3, 4) may comprise a local hub in the RVS device 10, operating per the Medical Body Area Network ("MBAN") in the 2360-2400 MHZ band allocated by the FCC (Federal Communications Commission). The vital sign data set may be transmitted from the hub to a remote location. The 40 MHZ band between 2360 MHZ and 2400 MHZ is allocated for "the development of the Medical Body Area Network (MBAN) devices . . . to provide a flexible platform for the wireless networking of multiple body transmitters used for the purpose of measuring and recording physiological parameters and other patient information or for performing diagnostic or therapeutic functions, primarily in health care facilities" by the Federal Communications Commission ("FCC") in a Report and Order and Further Notice of Proposed Rule Making (FCC 12-54) released May 24, 2012.

Figure 2:
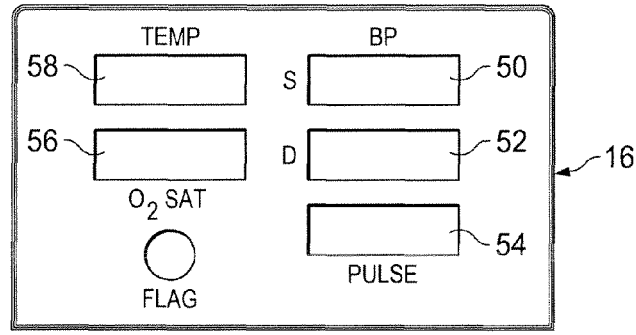
FIG. 2 illustrates a display panel of the embodiment depicted in FIG. 1.

FIG. 2 illustrates a display panel 16 for the embodiment depicted in FIG. 1, which may be implemented in any of several suitable technologies well known in the art. Preferably the display is adapted to reading out numerical values for the vital sign data. The outline 'boxes' represent the location of the numeric figures for respectively systolic 50 and diastolic 52 blood pressure, heart beat or pulse 54, blood oxygen saturation 56, and body temperature 58. The units of measurement may be imprinted in the display near the respective data numeric. For example, the blood pressure readings would be in mmHg, pulse in beats per minute (bpm), blood oxygen saturation in %, and body temperature in degrees F. (Fahrenheit) or C (Centigrade). The blood oxygen percent (%) figure indicates the percentage of hemoglobin in the blood that is "loaded" with oxygen ($O_2$). The display may further include an indicator symbol or icon representing an alert or 'flag' to indicate an anomalous reading of some kind, or a READY symbol or icon (not shown).

Figure 3:
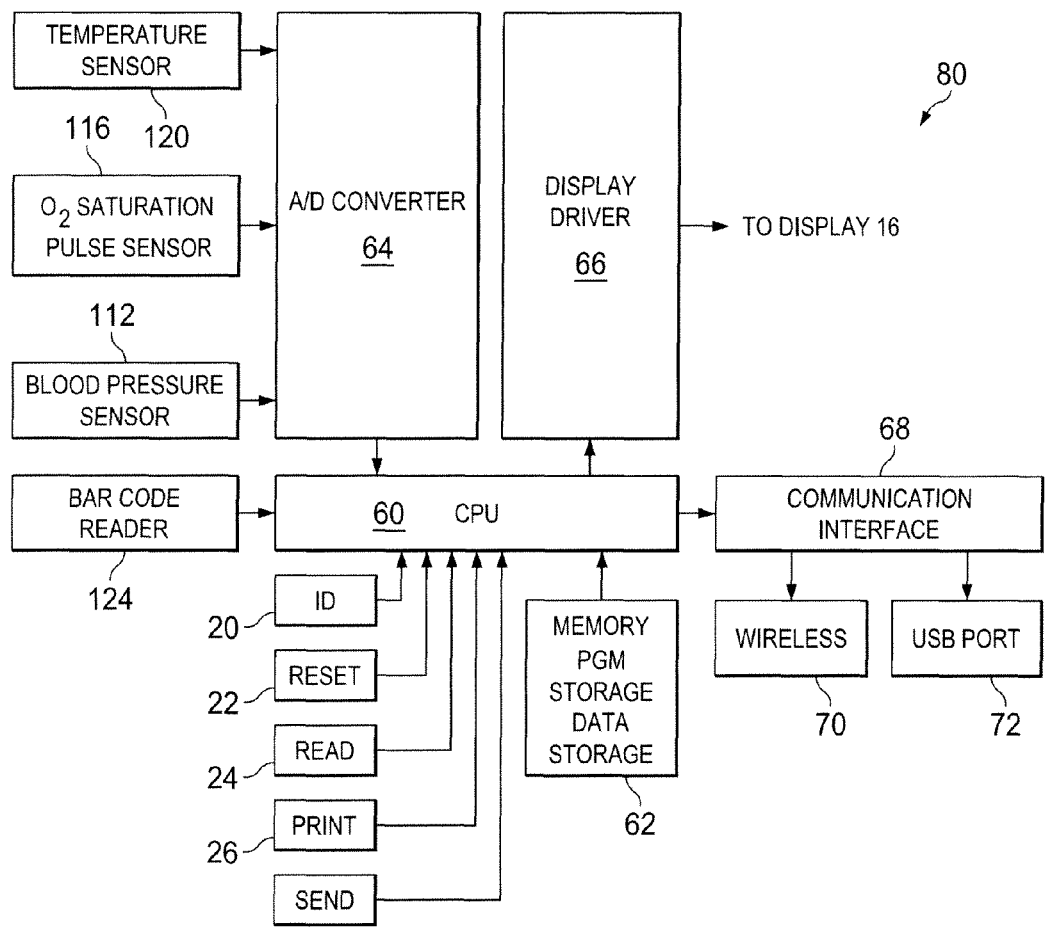
FIG. 3 illustrates a block diagram of one embodiment of an RVS device as depicted in FIG. 1.

FIG. 3 illustrates a block diagram of one embodiment of circuitry 80 contained in the RVS device 10 depicted in FIG. 1. The RVS circuitry 80 shown in FIG. 3 includes a CPU or processor 60 coupled to a non-volatile memory 62 for storing programs and data, a display driver 66 for reading out vital sign data on the display 16, an A/D (analog-to-digital) convertor 64, and a number of sensor input terminals coupled to the A/D convertor 64 for receiving data signals from the sensors for blood pressure 112, pulse oxygen saturation 116, and temperature 120. Also connected to respective inputs of the CPU 60 are buttons or touch pad icons for entering commands or data for operating the RVS device 10. These buttons include the ID 20, Reset 22, Read 24, Print 26, and Send 30 buttons. An input for receiving data from a bar code reader 124 may also be connected to an input of the CPU 60. The RVS instrument 10 may be preferably connected via a communication interface 68 in a network 106 coupled to a system such as an emergency room in a hospital or clinic 104 as will be shown and described in FIG. 4. The interface 68 may include a wireless transmitter 70 as previously described or utilize a wireless mesh network or any other suitable wireless link well known in the art. The interface may further include a USB connection 72.

Figure 4:
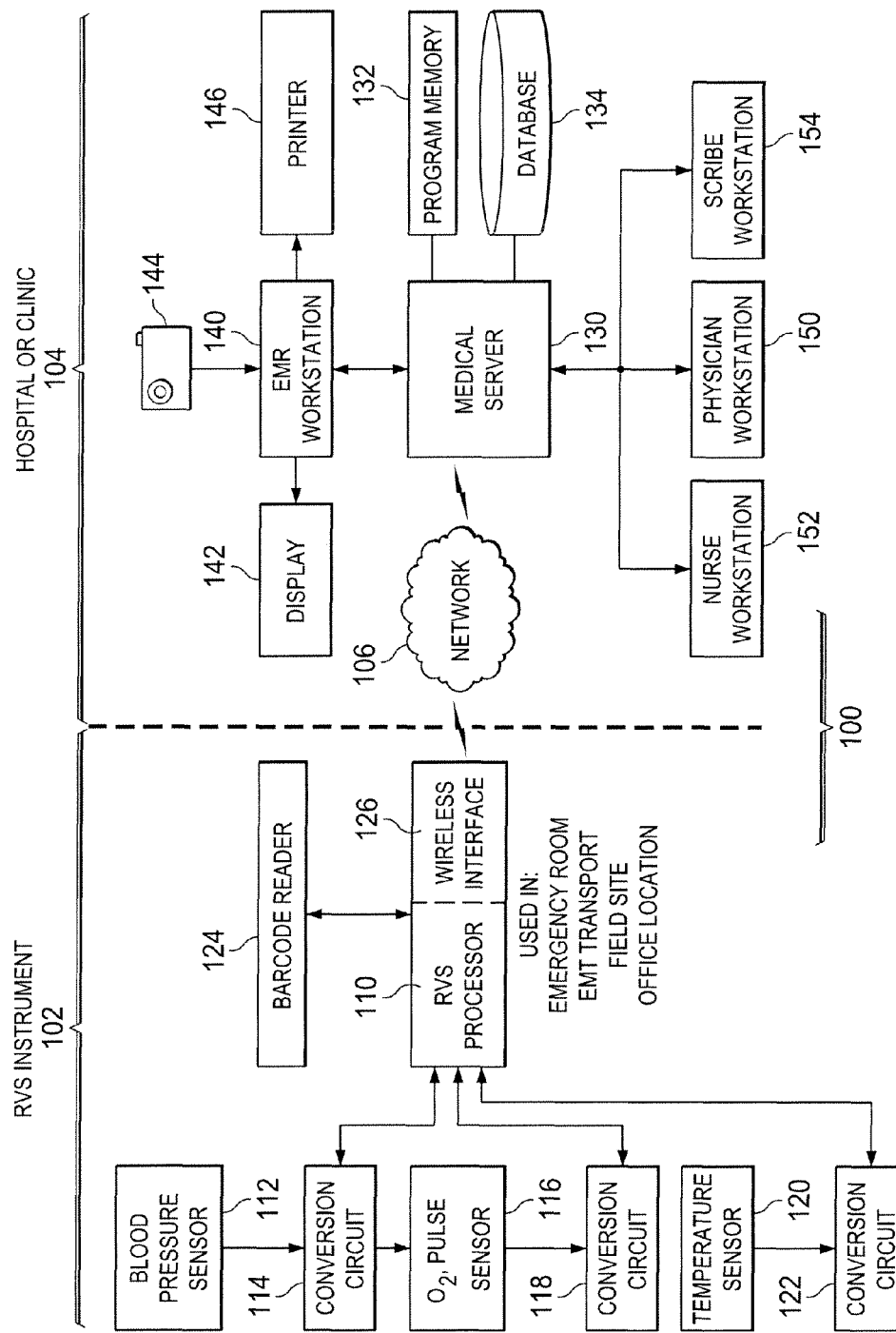
FIG. 4 illustrates a system block diagram depicting a typical system of use of the RVS device of FIGS. 1, 2, and 3 according to the present invention.

FIG. 4 illustrates a system block diagram depicting a typical system of use of the RVS device 10 of FIGS. 1, 2, and 3 according to the present invention. The diagram of the RVS system 100 is shown in two sections separated by the vertical dashed line. On the left is a simplified block diagram of an RVS device 102 (which is the same as the RVS device 10 of FIG. 1) including an RVS processor 110 shown coupled via a wireless interface 126 through a network 106 to a simplified block diagram of a hospital or clinic 104, shown to the right side of the vertical dashed line. Connected as inputs to the RVS processor 110 are a blood pressure sensor 112 and a conversion circuit 114 to match the sensor output signal to the input of the RVS processor 110. Similarly, the blood oxygen and pulse (pulse oximeter) sensor 116 is coupled via a conversion circuit 118 to the processor 110, and the temperature sensor 120 is coupled via its conversion circuit 122 to an input of the processor 110. In some embodiments a bar code reader 124 may be coupled to the RVS device 102 for entering patient identification data into the RVS device 102.

In the cuffless RVS device 10 described herein the sensor elements themselves (see, e.g., FIGS. 3 and 4, sensors 112, 116, 120), the sensors may preferably but not exclusively be optical proximity sensors well known in the art that employ light of a selected wavelength emitted by a light emitting diode (LED). The light signal, typically in the infra-red or visible portion of the spectrum, may be reflected from a portion of the vascular system such as a capillary bed or temporal artery, and the reflected signal detected by an photo detecting diode or transistor. Such reflected signals can correspond to the pressure changes in the capillary bed, providing a clear waveform of the heart rhythm. The detecting element may form part of a conversion or other circuit that may be integrated on a single chip. Thus, these elements can be manufactured in very small packages—on the order of a few millimeters square—thus enabling exceedingly compact sensors suitable for finger-tip applications. The small size of these sensor elements permits construction of RVS devices in a variety of small, portable, pocket-sized packages. The sensor elements may include amplifying, filtering, and other conversion circuitry to produce a signal compatible with external processing circuitry. The processing circuitry preferably includes suitable algorithms for interpreting the raw signal data produced by the sensors, including operations to average multiple readings taken over a span of time; to infer, from peak values of the pulse waveform the values of systolic and diastolic pressure within the capillary bed of a finger-tip; and further enabling estimation of the average time between peak events to determine pulse rate, etc.

The hospital or clinic 104 (representing a medical facility 104 herein) may include a medical server 130 having a wireless communication interface for connection with the network 106. Connected to the medical server 130 may be a program memory 132 and a database 134 for retaining electronic medical records. Also connected to the medical server 130 may be a network of care giver workstations including workstations for a physician 150, a nurse 152, and a scribe 154. The system 104 may further include an EMR workstation 140 for entering, accessing, displaying, printing, etc. patient data. A display 142, camera 144, and a printer 146 may all be connected to the EMR workstation 140. The workstations 140, 150, 152, 154 may be mobile or located in emergency room and triage settings to access the EMR system and to receive the data set output of the RVS device 102 via a wireless connection to the network 106.

The server 130, if accessed from the RVS device 102 or from a workstation that is connectable in the system network 106, may be called upon to perform some of the analysis of data obtained via the RVS device 102. In this way a variety of algorithms may be employed to assist the emergency room or triage care givers in determining the best next treatment step or process for the patient. The server 130 may access a variety of algorithmic programs stored in the database 134 for assessing the RVS sensor data sets. The server 130 and the work stations 140, 150, 152, 154 may further include facilities for printing reports to care givers to assist in communicating outcomes of the assessment and vital signs data.

The system diagram of FIG. 4 is intended to be broadly representative and not particularly descriptive of a specific computer network or system in a patient care center. Further, as experience with the data in numerous instances of its use accumulate, the ability to refine the use of the RVS becomes an important by-product that will naturally improve its utility. In one example, the system may be operable to construct tables of vital sign data for an individual patient that lists the vital sign data along with an initial assessment based on comparison of the individual vital sign data with established normal ranges and indicating via a readout in a portion of the table whether an out-of-range vital sign is irregular, abnormal, critical, etc. to indicate to a caregiver that special attention is required. Such condition may also be used to trigger an alert, alarm, or flag to call attention to a vital sign data set that includes at least one questionable reading. Such readings may initiate a flag or other alarm if the RVS device 10 or server 130 is programmed to provide this feature.

For example, program instructions provided in the system may include diagnostic analysis algorithms stored in the program memory for providing preliminary diagnosis alternatives derived from the sensor data set and the medical history data set. The program memory may further include a selection of standard vital sign profile charts stored in the program memory and accessible during processing of the sensor data set and the medical history data set. Program instructions operable in the processor of the server may also be provided to compare the vital sign data sets with standard vital sign profile charts and the medical history data set of the patient to produce a list of diagnostic alternatives for the patient connected to the portable instrument.

In the description that follows, whenever RVS device 10 is identified, either RVS device 10 or RVS device 102 is applicable.

Figure 5:
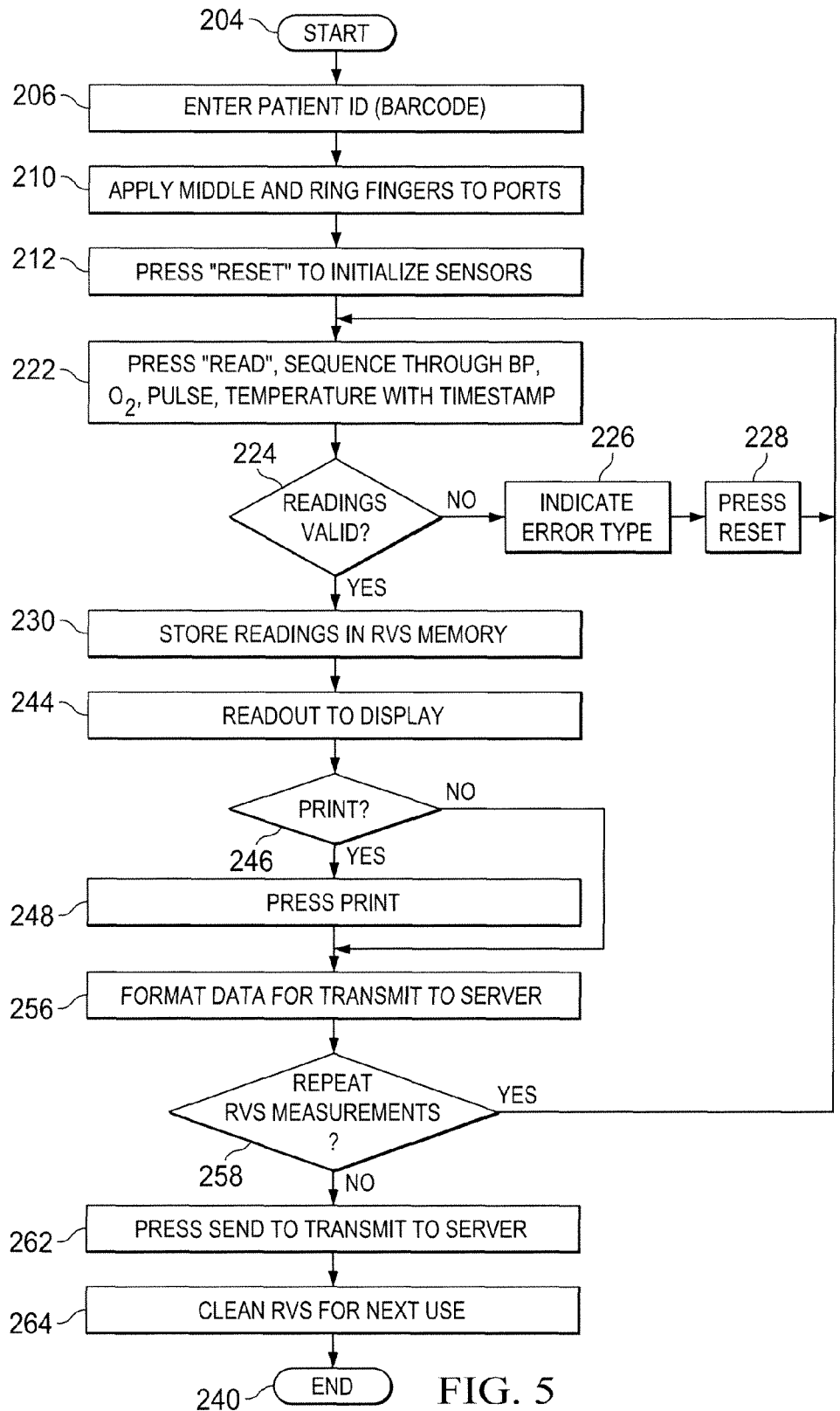
FIG. 5 illustrates a simplified flow chart of one embodiment of the RVS device in operation as a stand-alone vital signs instrument.

FIG. 5 illustrates a simplified flow chart of one embodiment of the RVS device 10 in operation as a stand-alone vital signs instrument. The reader will recognize the similarity between the process illustrated in FIG. 5 and the "Example of Use" set forth previously. The process starts at step 204 and advances to step 206 to enter patient ID into the RVS device 10 depicted in FIG. 1. Pressing the ID button 20 may be operable to condition the processor or CPU 60 (FIG. 2) to receive the ID information in barcode form. In step 210 the patient's middle and ring fingers are placed in contact with the areas designated Middle 34 and Ring 36 on the front panel 14 of the RVS device 10, followed by pressing the RESET button 22 on the device 10 to initialize the sensors. In the next step, the READ button 24 is pressed followed by the sequencing, automatically controlled by a program in the non-volatile memory 62 (FIG. 3), through the vital sign measurements for blood pressure, blood oxygen saturation, pulse, and body temperature. The measurement data may preferably include time stamp information.

Continuing with FIG. 5, the RVS device 10 tests the readings in step 224 to determine if they are valid readings, i.e., the measurement distinctly resulted in a definite numerical result. If the test indicates an error occurred—by a NO result in step 224—the type of error is indicated (such as but not limited to insufficient contact with sensor pad 34 or 36, residue on the contact pads 34 or 36, fingers not stationary, etc.) in step 226 and the user is directed to press the RESET button in step 228 and return to step 222, after correcting the reason for the error indication. Following valid readings in step 224 (indicated by YES) the readings are stored in step 230, read out on the display 16 (FIGS. 1 and 2) in step 244, and the process advanced to step 246. Step 246 provides access to the PRINT button 26 on the front panel 14. If the user desires a printed copy of the vital signs data the PRINT button 26 is pressed in step 248; if not, then the process advances to step 256 to format the vital signs data for transmitting it to a server in a network for use by caregivers. For example, the RVS device 10 may employ its wireless interface to connect to the network 106 and server 130 of FIG. 4 for storing in a database 134 so that caregivers in a hospital or clinic served by the network 106 may access the vital signs data from respective workstations 140 to 146 and 150 to 154. Transmission of the vital signs data stored in the RVS device 10 memory 62 occurs in step 258 when the user presses the SEND button 30 on the front panel 14. The RVS queries the user "Repeat RVS Measurements" in step 262. If YES, the flow advances to step 222 to repeat the sequence; if NO, the flow advances to step 264 to clean the RVS device 10 for the next use, and the routine ends at step 240.

Figure 6A:
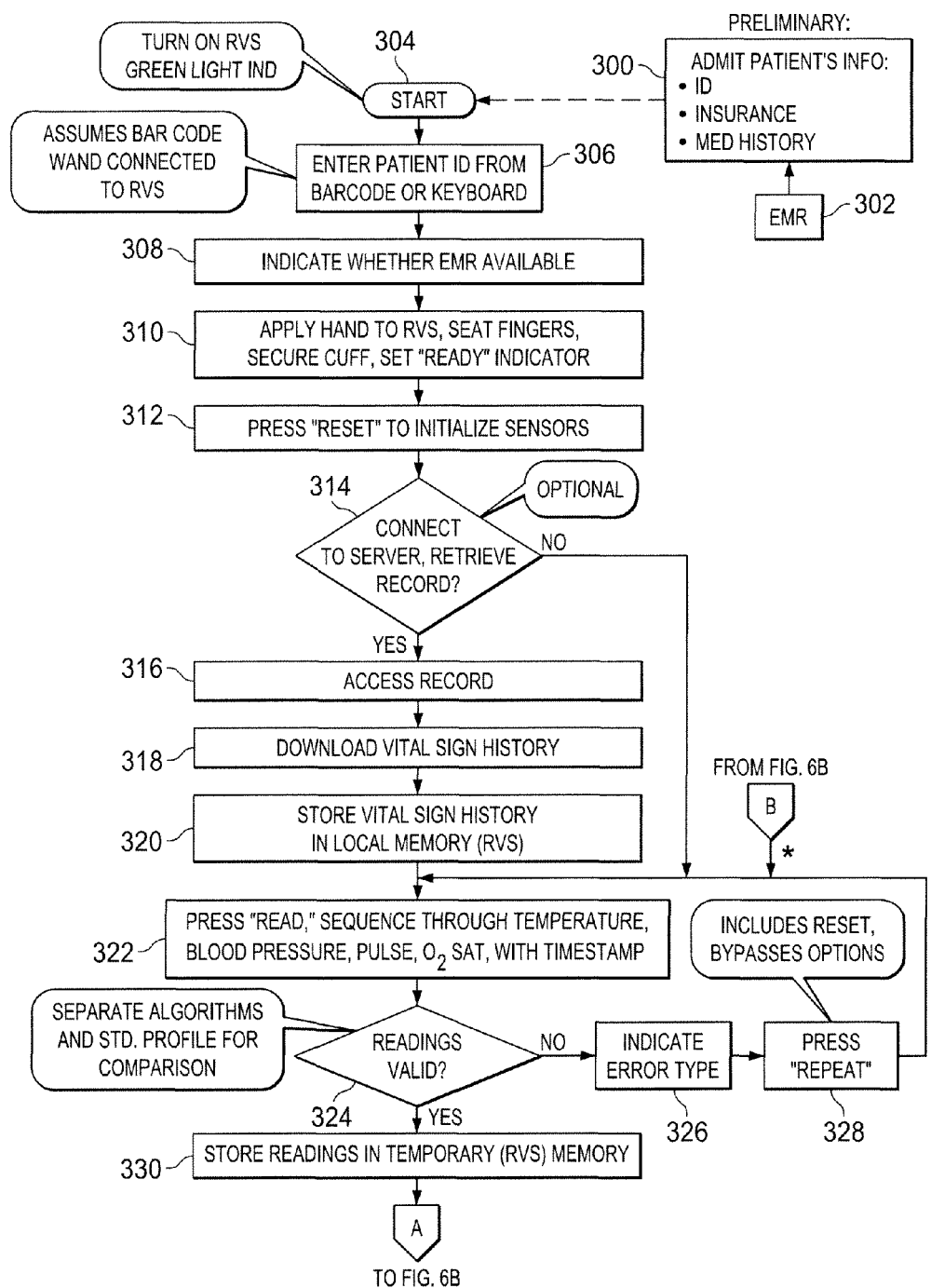
FIGS. 6A and 6B illustrates a flow chart diagram depicting one embodiment of the processes that may be carried out by the system and the RVS device shown in FIGS. 1 and 2.
Figure 6B:
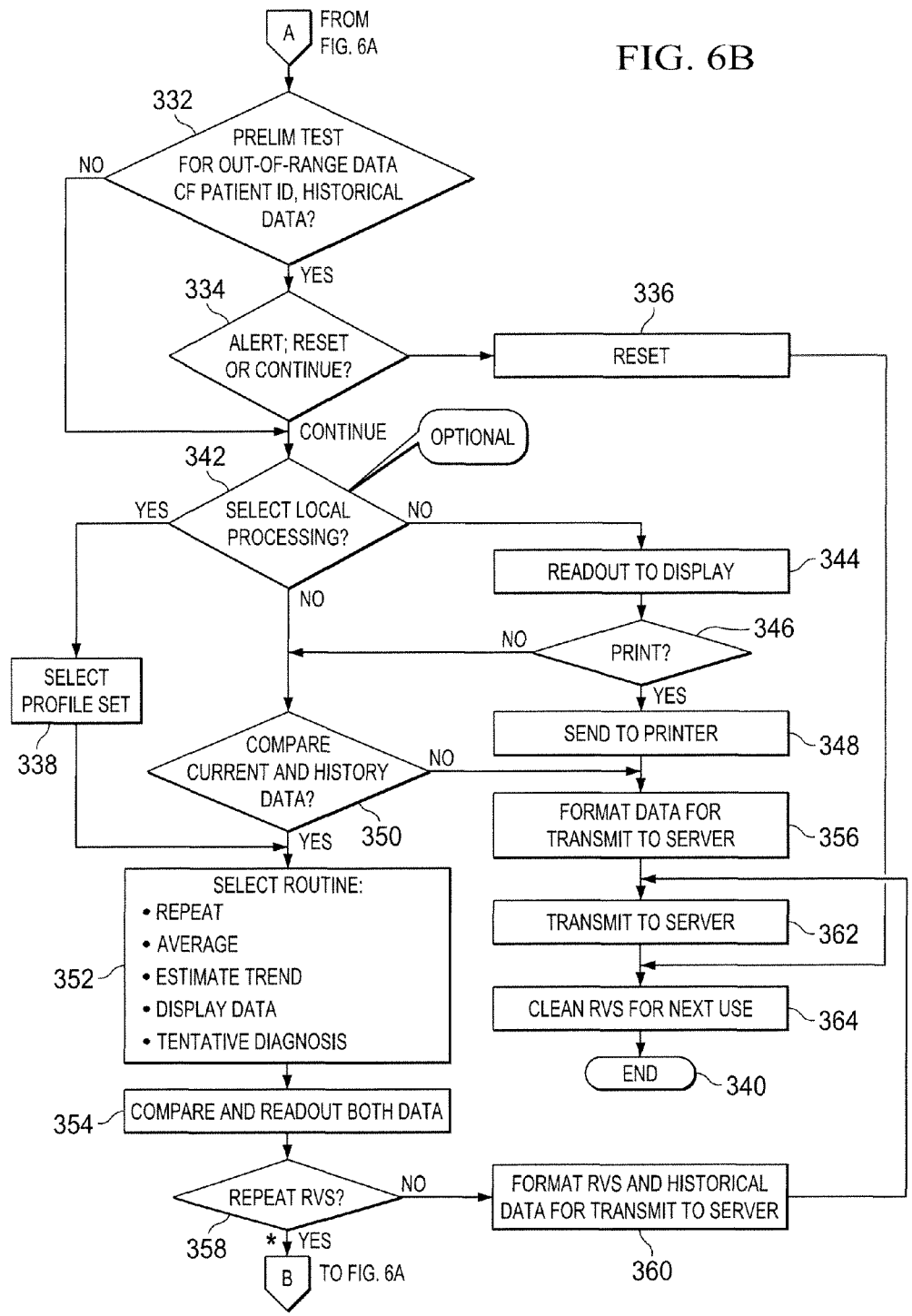

FIGS. 6A and 6B illustrates a more comprehensive flow chart diagram depicting one embodiment of the processes that may be carried out by the RVS device 10 of FIGS. 1-3 and the system 100 depicted in FIG. 4. The sequence may, of course vary from that shown depending on the particular architecture of the RVS device 10 (or RVS device 102) and its relationship with the hospital or clinic 104 and other elements in the system 100. As depicted, the process begins at step 304 to turn ON the RVS device 10, which may follow preliminary access to the EMR and other patient data in steps 300 and 302, including but not limited to identification, insurance, medical history and the like. This step 304 may be accompanied by illumination of the ON indicator light 32 (See FIG. 1). The entry point for patient identification may be via a bar code reader (for reading a patient's bracelet ID device having a bar code) connected to the RVS device 10 and a check, as in step 308 to determine if the EMR data is available. In an alternate embodiment, a keyboard or keypad on the RVS device 10 (if so equipped) may be used to enter a patient ID.

At step 310 the patient's hand is applied to the RVS device 10, which may be configured as a small portable unit hanging from the bedside or gurney frame, a pocket-sized instrument, or a glove-like device. In any case placing the hand on the front panel 14 of the RVS device 10, or attaching the RVS device 10 to the patient's hand if so configured, or a B/P cuff to the patient's arm in step 310, setting a READY indicator (not shown in FIG. 1 or 2 for clarity, but may be a signal on the display 16), followed by pressing the RESET button 22 to initialize the sensors (in step 312) prepares the RVS device 10 to sense the respective vital signs data when the READ button 24 is pressed at step 322 as will be described.

Continuing with FIG. 6A, a test query provides in step 314 to select connecting to the server 130 (in the system 100 of FIG. 4) to retrieve a patient record. If it is known that the patient may have a record in the facility 104 then the flow is along the YES path to access the record in step 316, download the vital sign history (for example) in step 318, and store the vital sign history in the local non-volatile memory 62 of the RVS device 10 in step 320. If, on the other hand a patient's vital sign history or other pertinent medical record is not in the database 134 of the facility 104, the flow advances along the NO path to step 322.

Step 322 initiates the measurement process in the RVS device 10 when the READ button 24 is pressed to "read" the outputs of the sensors for the vital signs of the patient. Here again, the sequence may be to perform a measurement of blood pressure (both systolic and diastolic values), blood oxygen saturation, pulse, and body temperature in this example. The measured values appear in the display 16 in the designated regions of the display. Blood pressure is recorded as two values, the systolic (contraction of the heart) and diastolic (relaxation of the heart), blood oxygen saturation is indicated as a percentage (%) figure, pulse is indicated in beats per minute (bpm), and body temperature in degrees Fahrenheit (° F.) or, in some units if the scale is selectable, degrees Centigrade (° C.). In step 322 the vital sign data may be time stamped to enable correlation of the vital sign data with the passage of time form the first measurement to later measurements on the same patient. This information is useful in monitoring trend lines—patterns of data that may in themselves indicate medical conditions not otherwise detectable with a single set of vital sign data.

Continuing with FIG. 6A, a check is made at step 324 for valid readings, and if NO, an error occurs, the error type may be indicated in step 326, the reading discarded. The flow then advances to block 328 where the READ button 24 is pressed again (or, in an alternate embodiment, a REPEAT button (not shown) is pressed to return the flow to the input of step 322 to read the parameters again, preferably after re-checking the placement of the patient's finger on the sensor pads 34, 36. If the readings are determined valid in step 324, the flow advances along the YES path to step 330.

Proceeding with FIG. 6B, after storing the readings in the RVS memory at step 330 (FIG. 6A), the flow may advance to perform a preliminary test for out-of-range results in step 332 and comparing it with historical data from, e.g., the EMR if it is available. If an out-of-range parameter is identified, indicating a possible health-related alarm situation, an ALERT may be issued in step 334, followed by proceeding to RESET the device in step 336 and to END the routine in step 340. Note that in step 332, the out of range data may be determined with reference to a selected profile table of values stored in memory according to patient's age, gender, overall physical appearance, type of injury or disease condition, etc. An ALERT may be indicated by visual or aural means, such as an indicia on the display 16 or an annunciator built into the RVS device 10, neither of which are shown in the figures.

Alternatively, if the choice is to continue, the flow moves forward to step 342 (an optional step) to decide whether to select local processing of the sensor data if it is within normal ranges for the patient. If the decision is to select local processing in step 342, a profile set corresponding to the patient is selected in step 338 and the process may call up a selected routine in block 352 from a list of processing routines that may include, for example, Repeat the measurement; Average the data from the measurements; Estimate a trend in the measurements; Display the data; or Make a tentative diagnosis. From block 352 the flow advances to step 354 to compare and readout both the original and the processed data results. The care giver may then request to REPEAT the RVS test in step 358 and return to step 322 via the path marked with an asterisk (*) or, if no repeat is needed, to advance to step 360 to format the RVS and historical data for transmission to the server or hub of the RVS device in step 362, after which the process ENDs at step 340.

Returning to step 342, if local processing was declined, the flow proceeds to step 344, which provides for printing out a paper copy of the results of the RVS tests in steps 346 and 348. Following printing the flow advances to step 356 to format the data for transmission to the server 130 in the facility 104, and transmit the vital sign data to the server 130 in step 362. Again, the current and historical data may be compared in step 350, and if YES then followed by the step 352 to select a routine for analysis of the parameter data reported by the RVS device 10. If the choice is made in step 346 to decline a comparison of current and historical data for the patient, the flow follows the path to format the data for transmission to the server in step 356 and send the transmission in step 362. Thereafter, the process ENDs in step 340 after cleaning the RVS device 10 in step 364 for the next use as previously described.

One of the optional subroutines occurs at step 314 in FIG. 6A, whereupon the care giver may opt to access the EMR in step 316 and download the vital sign history of the patient in step 318. If this option is selected, the vital sign history may be stored in the local memory 362 of the RVS device 10 in step 320. The flow then returns to step 322 described previously.

In notes that are placed adjacent several of the steps in FIG. 3, explanatory details are provided to assist understanding. The START block 304 commences with the care giver turning ON the RVS accompanied by illumination of, for example, a green light indicator. The bar code reader mentioned in conjunction with step 306 is an optional feature. During step 328, this step may include other actions such as RESET, BYPASS or other options. In the validity check step 324 it may be necessary to check that separate algorithms or profile set for checking the validity are appropriate for the patient.

Figure 7:
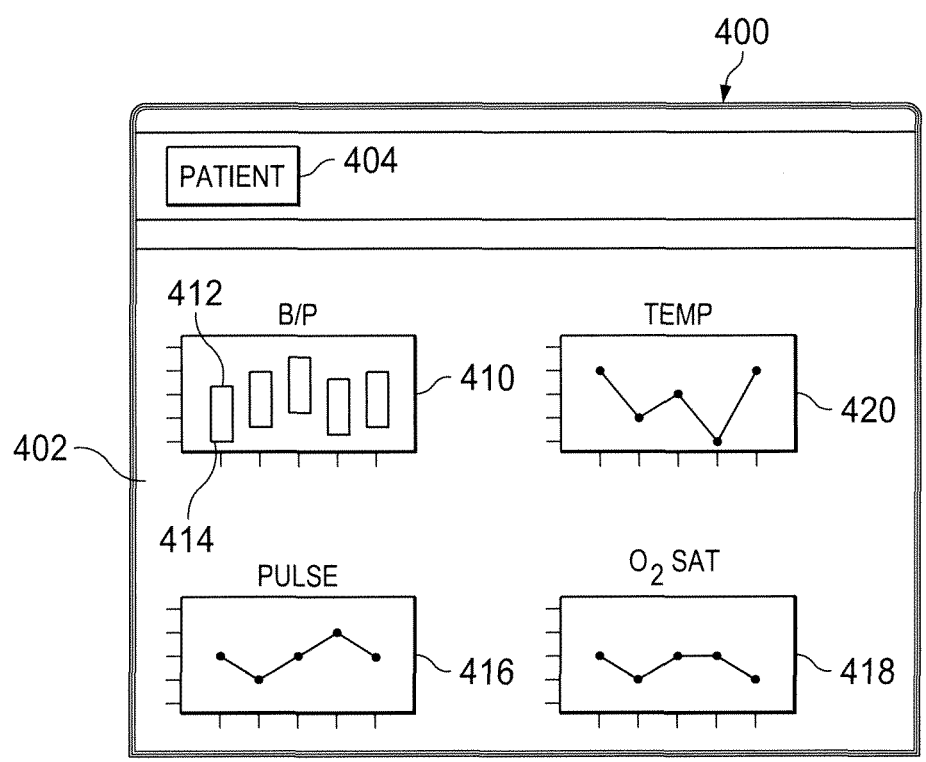
FIG. 7 illustrates an alternate embodiment of an RVS device display for use with the system embodiment of FIGS. 6A and 6B according to the present invention.

FIG. 7 illustrates one example of a typical vital signs profile chart or display of the type that may be used and displayed by a display 142 coupled to the server 130 in the system of FIG. 4 in reporting the results of measurements performed by the RVS device 10. The display 142 displays a graphic image 402 includes a patient identifier 404 and sections configured as separate graphs or plots of blood pressure 410, pulse 416, blood oxygen saturation 418, and body temperature 420. The blood pressure graph 410 includes a sequence of histograms showing the systolic 412 and diastolic 414 values recorded at specified times marked on the horizontal axis. The vertical axis is preferably marked in units of mmHg. The graph for pulse 416 may display the pulse recorded at the same times as the blood pressure readings in graph 410, on a vertical scale marked in beats per minute. Similarly, the graph for blood oxygen saturation ("$O_2$ Sat") may be recorded at the same time intervals as the blood pressure and pulse, with their percentage values corresponding to the percent numbers marked on the vertical scale. Finally, the body temperature graph 420, with its vertical scale marked in degrees F. or degrees C. (for example, degrees F. on the left vertical axis and degrees C. marked on the right vertical axis) may be shown at each of the same times that the other vital sign data is displayed. In this way each graph displays a sequence of readings over time at intervals marked on the horizontal axis, allowing trends to be spotted and correlations identified among the individual vital signs. Such information about trends or patterns or correlations may disclose particular conditions of interest to the caregiver or physician.

In a hypothetical example of the use of vital sign data provided by the RVS device 10, such as for a 27 year old male patient of average height and weight and apparently in "great" physical condition, four sets of vital signs parameters may be obtained. The state of the patient may be estimated by an algorithmic process and estimated according to the data reported by the RVS device 10. In this example the state may be identified as Normal (regular/normal, good condition), Abnormal (not normal/alarming, cause for concern), Critical (Abnormal for several minutes and or continue to worsen), and Irregular (sensors disconnected, providing false readings?). These "State" conditions may thus be interpreted as an initial, preliminary assessment to draw the attention of the care giver to the RVS results. As additional RVS readings are taken at selected intervals, a pattern (such as provided by the display of FIG. 7) of "states" may emerge to clarify these initial assessments or to indicate the effects of treatment. These chart sets may be stored in the local memory 62 of the RVS device 10 as described in FIG. 6A, step 320.

CONCLUSION

To summarize, the present invention provides the ability to (1) take all vital sign readings at one time, and repetitively at intervals and locations during the patient's movement through the hospital system, thus providing a continuous, timely record; (2) format the vital sign data and send it wirelessly to the EMR system for ready access and retrieval as needed by care givers; (3) provide automated preliminary analyses of the data along with other patient information to determine or indicate the most likely possible explanations of the illness or injury experienced by the patient; (4) assist the hospital determine the tests to be ordered to minimize lost time; (5) reduce the number of vital sign data input errors by formatting the data and transmitting it directly from the RVS instrument; and (6) ensure correct association of the patient ID and vital sign data.

The foregoing descriptions and illustrations of embodiments of the invention are representative examples of possible implementations of the concept of a small portable instrument for rapidly and accurately measuring at least four vital signs of a patient experiencing trauma or illness, whether mild or severe, and of the transmission and integration of the instrument's data via communication links with the computer system and network of a medical treatment location whether it be a hospital, clinic, triage center, temporary field hospital, and the like to medical personnel engaged in treating patients, particularly in an "emergency department" setting. The scope of the invention is not limited to these particular illustrations but may include various combinations thereof that may occur to persons of skill in the art. The concept of the invention is a precursor to a system of initial diagnosis that relies on rapid and accurate vital signs data and algorithms for analysis of the vital signs data, the circumstances and appearance of the patient, and other patient medical record data to determine most likely avenues for treatment and/or further tests. When a patient is brought to an Emergency Room time is often of the essence, and processing of incoming cases is often complicated by the number of patients awaiting examination and evaluation. The present invention is directed toward apparatus, and systems and methods for accurate and rapid assessment and diagnosis of patient illness or injury leading to appropriate treatment as soon as possible.

While the invention has been shown in only one of its forms, it is not thus limited but is susceptible to various changes and modifications without departing from the spirit thereof.

What is claimed is:

1. A portable instrument for providing rapid measurements of vital signs, comprising:
   a handheld, cuffless device operable during brief touch contact with one hand of a patient undergoing emergency health evaluation to produce a vital sign data set for the patient;
   an assembly of touch contact sensors in the device for measuring and outputting measurement values for blood pressure, pulse, blood oxygen saturation, and body temperature;
   a processor in the device operable under programmed control to receive and process the measurement values output by the sensors and produce the vital signs data set;
   a display controlled by the processor for reading out numerical values of the vital sign data set; and
   a wireless interface coupled to the processor for transmitting the vital sign data set to an electronic medical record in a remote database.

2. The instrument of claim 1, further comprising:
   a single housing having finger stations for sensing by touch contact the patient's blood pressure, pulse, blood oxygen saturation, and body temperature.

3. The instrument of claim 1, further comprising:
   a cuffless sensor for measuring by touch contact the patient's systolic and diastolic blood pressure;
   a pulse oximeter sensor for measuring by touch contact the patient's pulse and blood oxygen saturation;
   a thermometer for measuring by touch contact the patient's body temperature; and
   at least one analog-to-digital convertor circuit for converting data output by each sensor for processing by the processor.

4. The instrument of claim 1, wherein the assembly of touch contact sensors comprise:
   optical proximity sensors operable to detect changes in blood flow through the capillary bed of a patient's finger tip; and
   operable to detect body temperature of a temporal artery.

5. The system of claim 1, wherein the processor comprises:
   a programmable central processing unit including, a memory for program storage; and
   at least program instructions for processing the sensor data and controlling the wireless interface.

6. The instrument of claim 5, wherein the wireless interface comprises:
   a wireless transceiver controlled by the processor operable according to a communications protocol to communicate with a remote server via a wireless network.

7. A system for emergency medical diagnosis comprising the portable instrument of claim 1, further comprising:
   a server connected to a program memory and a database for electronic medical records, and operable in a medical facility network of caregiver work stations and at least one emergency room workstation.

8. The system of claim 7, wherein the emergency room workstation comprises:
a computer having a display and a printer coupled thereto.

9. The system of claim 7, further comprising:
diagnostic analysis algorithms stored in the program memory for providing preliminary diagnosis alternatives derived from the sensor data set and the medical history data set.

10. The system of claim 9, further comprising:
a selection of standard vital sign profile charts stored in the program memory and accessible during processing of the sensor data set and the medical history data set.

11. The system of claim 10, wherein:
program instructions operable in the processor of the server to compare the vital sign data sets with standard vital sign profile charts and the medical history data set of the patient to produce a list of diagnostic alternatives for the patient connected to the portable instrument.

12. The system of claim 7, wherein the caregiver workstations comprise:
a first program accessible from the caregiver work station for analyzing initial and subsequent vital sign data obtained at intervals of time by the portable instrument to enable identification of trends in the vital sign data.

13. The system of claim 7, comprising:
a second program in the caregiver work station for displaying in a single screen display to a medical practitioner trends over time in both the vital sign data and the patient's historical data.

14. A portable instrument for providing rapid measurements of vital signs, comprising:
a handheld, cuffless device enclosed in a housing and operable during brief touch contact with a patient undergoing emergency health evaluation to produce a vital sign data set for the patient;
an assembly of touch contact sensors on the surface of the housing configured for measuring and outputting from the touch contact of fingers of one hand of the patient thereon the vital sign data set for blood pressure, pulse, and blood oxygen saturation;
at least one analog-to-digital convertor circuit coupled to outputs of the touch contact sensors for converting its vital sign data output for processing by a processor;
a processor in the device operable under programmed control to receive and process the vital sign data output by the touch contact sensors and produce the vital signs data set;
a display controlled by the processor for reading out numerical values of the vital sign data set;
an assembly of touch contact controls on the surface of the housing and coupled to the processor for entering commands for reading, specifying vital sign data to be measured, and sending vital sign data; and
a wireless interface coupled to the processor for transmitting the vital sign data set to an electronic medical record in a remote database.

15. The instrument of claim 14, further comprising:
the display configured for displaying patient identification information;
a blood pressure graphical plot includes at least one histogram depicting systolic and diastolic values; and
separate graphical plots for displaying the values of the vital sign data set for pulse, blood oxygen saturation, and body temperature.

16. The instrument of claim 14, further comprising:
a receptacle for connecting a bar code reader to input patient identification information to the instrument.

17. The instrument of claim 14, further comprising:
a USB port for supplying a communications link from the instrument to an electronic medical record in a remote database.

18. The instrument of claim 14, wherein the assembly of touch contact sensors comprises:
at least one optical proximity sensor operable to detect changes in blood flow through a patient's capillary bed of the patient's finger tip; and
a touch contact sensor operable to detect body temperature of a temporal artery of the patient.

19. The instrument of claim 14, wherein:
the housing is configured for carrying in a caregiver's pocket.

* * * * *